United States Patent [19]
Tanagho et al.

[11] Patent Number: 4,703,755
[45] Date of Patent: Nov. 3, 1987

[54] CONTROL SYSTEM FOR THE STIMULATION OF TWO BODILY FUNCTIONS

[75] Inventors: Emil A. Tanagho, San Rafael; Richard A. Schmidt, San Francisco; Curtis A. Gleason, Palo Alto; Tom F. Lue, Millbrae, all of Calif.

[73] Assignee: The Regents of the University of California, Berkeley, Calif.

[21] Appl. No.: 837,706

[22] Filed: Mar. 7, 1986

Related U.S. Application Data

[62] Division of Ser. No. 611,836, May 18, 1984, Pat. No. 4,607,639.

[51] Int. Cl.$^4$ .............................................. A61N 1/36
[52] U.S. Cl. .............................................. 128/419 R
[58] Field of Search .............................. 128/421–423

[56] References Cited

U.S. PATENT DOCUMENTS

| 3,822,708 | 7/1974 | Zilber | 128/419 R |
|---|---|---|---|
| 3,851,651 | 12/1974 | Icenbice, Jr. | 128/422 |
| 3,893,463 | 7/1975 | Williams | 128/421 |
| 3,920,025 | 11/1975 | Stasz et al. | 128/423 R |
| 4,014,347 | 3/1977 | Halleck et al. | 128/422 |
| 4,019,518 | 4/1977 | Maurer et al. | 128/419 R |
| 4,024,875 | 5/1977 | Putzke | 128/423 R |
| 4,390,023 | 6/1983 | Rise | 128/421 |
| 4,398,537 | 8/1983 | Holmbo | 128/420 R |

Primary Examiner—William E. Kamm
Attorney, Agent, or Firm—Phillips, Moore, Lempio & Finley

[57] ABSTRACT

A system for controlling bladder evacuation includes first and second implanted stimulation systems having electrodes respectively positioned on nerves controlling external sphincter and bladder functions, and an electronic control system which operates to generate and transmit electrical sphincter stimulation pulses to the first stimulation system. When it is desired to evacuate the bladder, a switch is closed causing the electronic control system to discontinue the external sphincter stimulation and, after a predetermined delay, to generate and transmit electrical bladder stimulation pulses to the second stimulation system. After a predetermined time, the bladder stimulation is automatically stopped. After another predetermined delay, the electronic control system resumes the generation and transmission of sphincter stimulation pulses to the first stimulation system.

11 Claims, 17 Drawing Figures

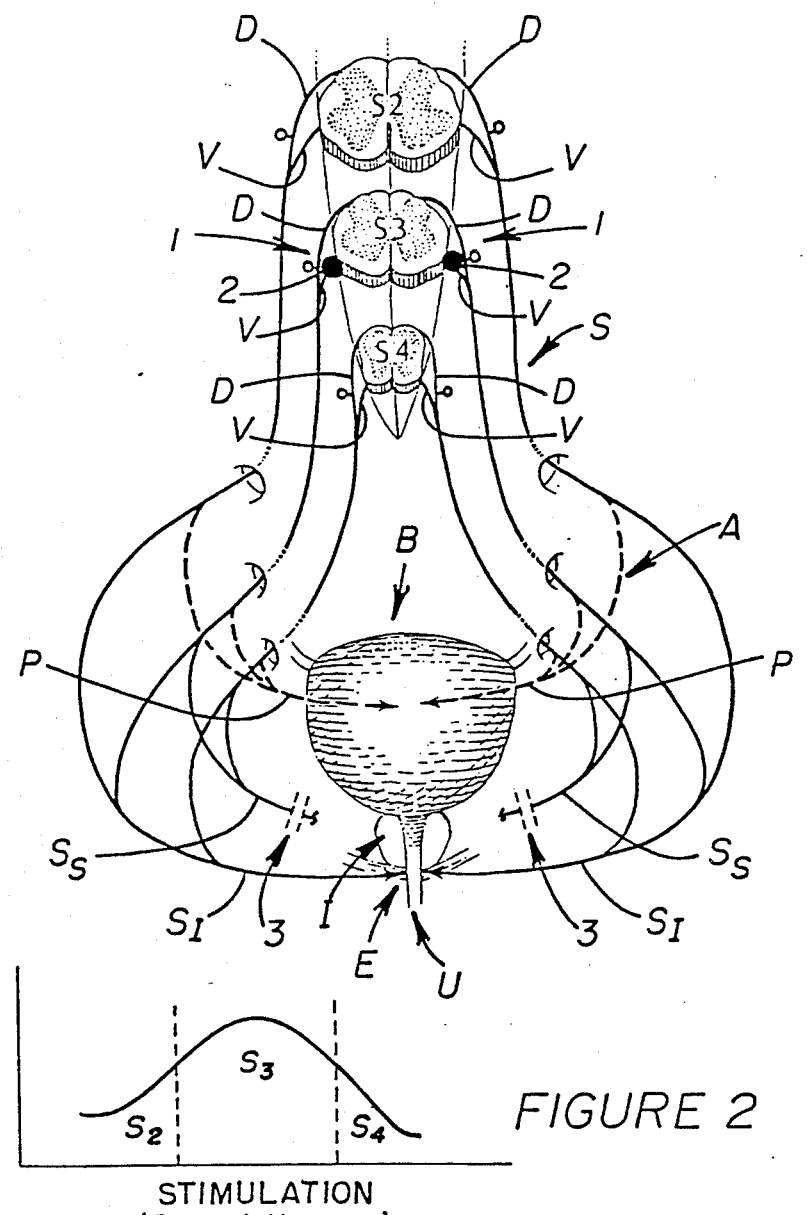

FIGURE 13
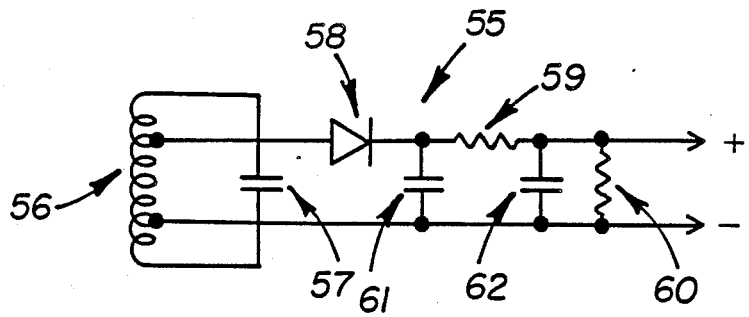
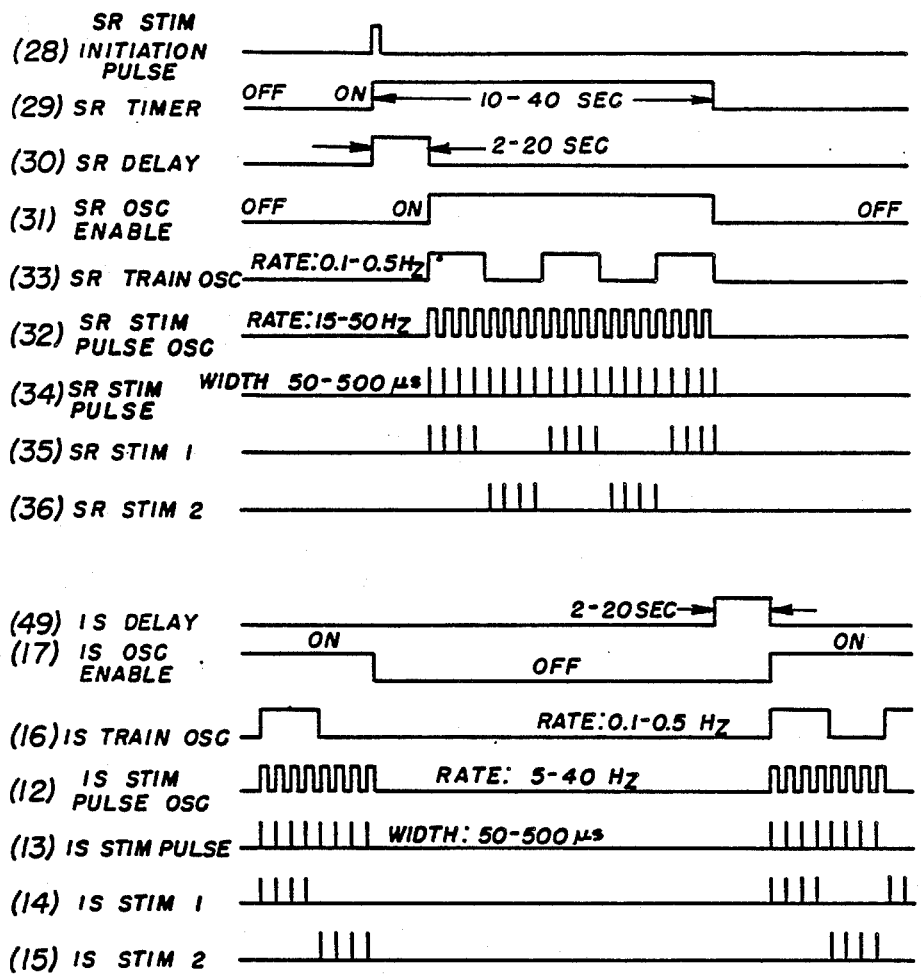
SR = SACRAL ROOT
IS = INFERIOR SOMATIC
OSC = OSCILLATOR
FIGURE 14

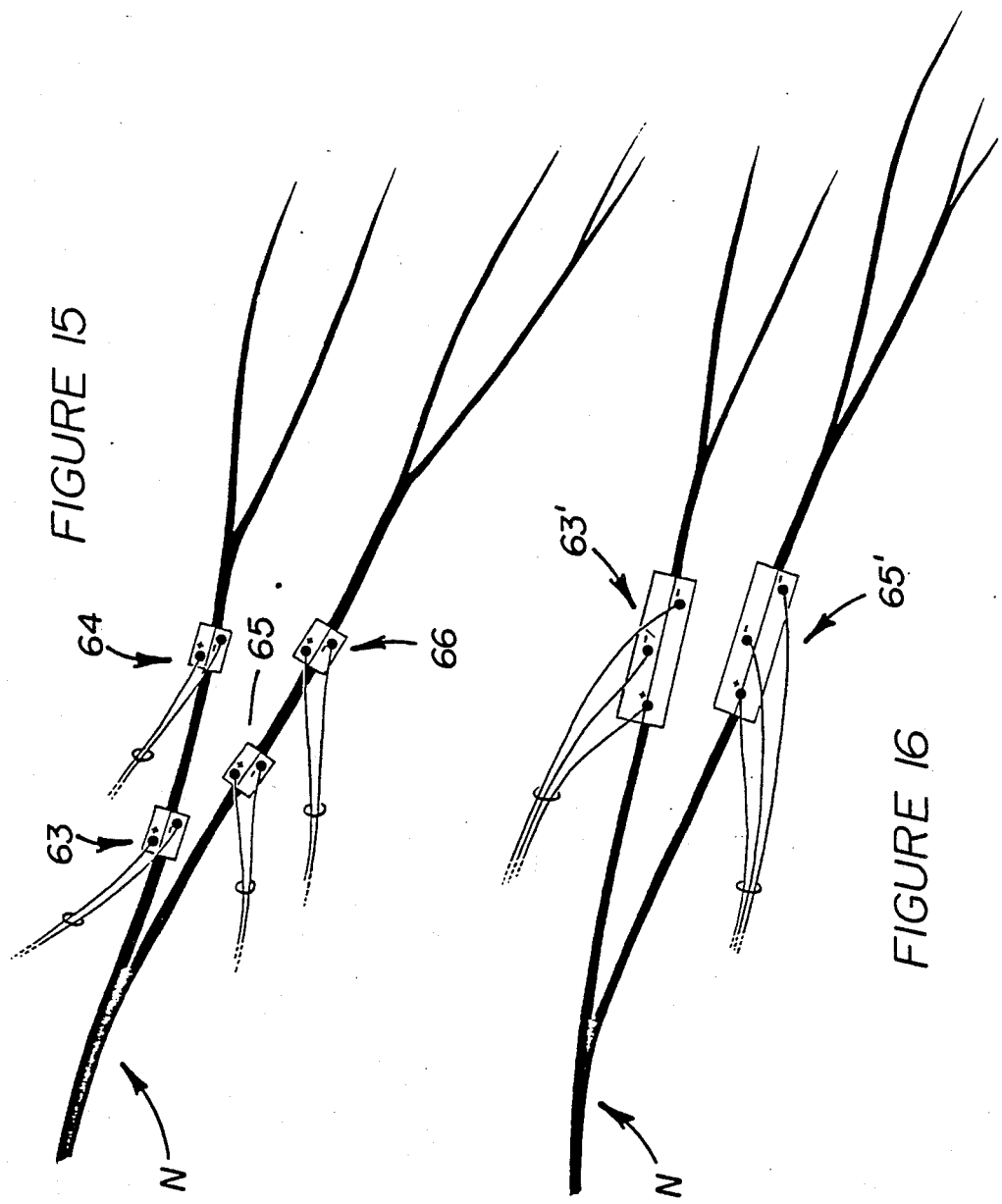

CONTROL SYSTEM FOR THE STIMULATION OF TWO BODILY FUNCTIONS

This is a division of Ser. No. 611,836 filed May 18, 1984, and issued on Aug. 26, 1986, as U.S. Pat. No. 4,607,639.

TECHNICAL FIELD

This invention relates generally to a system for closely controlling the function of an organ and, more particularly, to the placement of one or more electrodes at strategical anatomical locations on critical nerves of a patient to control one or more functions of a bladder.

BACKGROUND ART

Various medical patients, such as quadriplegics, exhibit involuntary control over their bladder and related functions, such as bowel evacuation. Although vesicostomy or artificial sphincter implanted around the urethra are commonly used to provide partial control over the evacuation function of the bladder and continence, these solutions have drawbacks well known to those skilled in the medical profession and arts. Other patients who achieve a modicum of control over their bladder functions are equally in need of a system to rehabilitate their nerve and muscle dysfunctions.

Applicants are unaware of any prior art that suggests a method and system wherein electrodes are precisely positioned on critical nerves and in various combinations on a particular patient for physiologically stimulating the nerves in a preselected manner for the purpose of controlling the continence and evacuation of a bladder, or for stimulating such nerves to correct a dysfunction by neurostimulation. Applicants are also unaware of any successful operative procedure that further includes the identification of various levels and components of such critical nerve fibers and their selective separation and/or isolation for the purpose of controlling muscle contractions and pain impulses.

For example, U.S. Pat. No. 4,406,288 discloses a system that purportedly conditions pelvic floor musculature by means of neurostimulation for the purposes of controlling urinary loss. Such system includes excitation apparatus for applying electrical pulses to electrodes implanted in the abdominal region or to a plug positioned in an anus. The plug contacts the sphincter muscle of the anus for the alleged purpose of inhibiting bladder contraction in response to excitation of the plug. U.S. Pat. No. 3,941,136 discloses a similar system.

DISCLOSURE OF INVENTION

This invention overcomes the above, briefly described prior art problems by providing a system for controlling the continence and evacuation of a bladder and other organs innervated by the pelvic nerves. The term "controlling" as used herein not only includes the selective control of the bladder's evacuation and related functions on a continuous basis, but further includes isolated or periodic control of the bladder's function for diagnostic or rehabilitation purposes, e.g., neuromodulation of muscular behavior to rehabilitate muscular dysfunction. The term "organ" as used herein broadly means an independent part of the human body that performs a special function or functions, including visceral organs such as the bladder, bowel and colon and associated sphincters and cuffs.

In its broadest aspect, the system of this invention comprises an electronic control for sending electrical stimulation signals to first and second stimulation systems implanted in a body, the stimulation systems having electrodes positioned, respectively, on nerves controlling two different bodily functions, the electronic control system functioning to send stimulation signals normally to the first stimulation system. At a desired time, the electronic control will cease sending stimulation signals to the first stimulation system and, after a predetermined delay, will send stimulation signals to the second stimulation system. After a predetermined period, the electronic control will automatically cease sending stimulation signals to the second stimulation system and, after another predetermined delay, will resume sending stimulation signals to the first stimulation system.

In another aspect of the invention, the stimulation signals are time spaced bursts of pulses.

In a further aspect of the invention at least one of the stimulation systems has two electrodes positioned on different nerves controlling the same bodily function, and the electronic control sends time spaced bursts of pulses to the two electrodes, with the bursts of pulses being alternately sent to each of the electrodes.

BRIEF DESCRIPTION OF THE DRAWINGS

Other advantages and objects of this invention will become apparent from the following description and accompanying drawings wherein:

FIG. 1 schematically illustrates the pelvic plexus region in a human, including the nervous system for controlling bladder evacuation and related functions, and further illustrates a first operative procedure for controlling such functions;

FIG. 2 schematically illustrates a stimulation-response curve of bladder contraction in response to stimulation of the S2, S3 and S4 sacral nerves;

FIG. 13 schematically illustrates a typical electronic circuit for use in an implantable receiver of the FIG. 12 micturition control system;

FIG. 14 diagrammatically illustrates electronic signals and their time relationship for the FIG. 12 micturition control system;

FIG. 15 illustrates an electrode arrangement including pairs of electrodes attached to separate nerve fibers and adapted for use with the FIG. 12 control system;

FIG. 16 is a view similar to FIG. 15, but illustrates a multiplicity of active electrode contacts on single electrodes.

BEST MODE OF CARRYING OUT THE INVENTION

GENERAL DESCRIPTION

Figure 3:
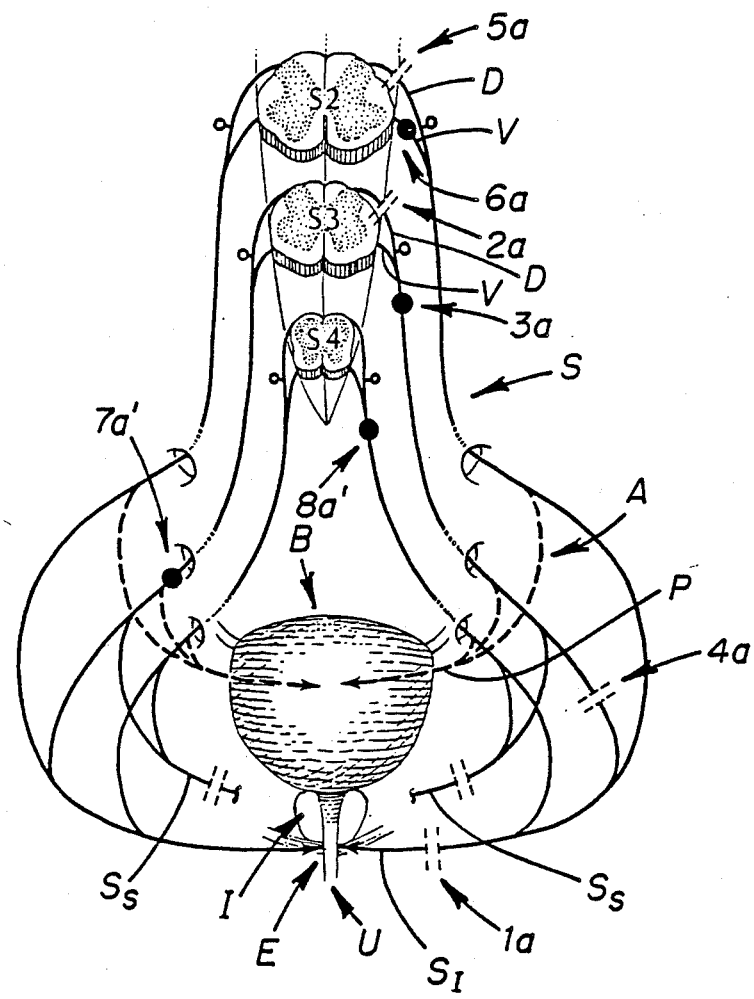
FIGS. 3 and 4 are views similar to FIG. 1, but illustrate additional operative procedures for controlling bladder evacuation and related functions.

FIG. 1 schematically illustrates the pelvic plexus region of a human, including the nervous system for controlling bladder evacuation and related functions. The nervous system includes a somatic nerve system of fibers S and an autonomic nerve system of fibers A, finding their immediate origin at sacral segments S2, S3 and S4 of the spinal cord and sacrum, i.e., the triangular bone positioned below the lumbar vertebrae and comprising five fused sacral vertebrae that are wedged dorsally between the two hip bones. As illustrated in FIG. 2, the main nerve supply to the detrusor muscle of a bladder B emanates primarily from sacral segment S3, a lesser amount from sacral segment S2, and a still lesser amount from sacral segment S4, i.e., "response" refers to bladder response.

One aspect of this invention is directed to a method for controlling the evacuation of bladder B by first identifying the anatomical location of at least one nerve or component thereof that controls at least one function of the bladder, e.g., continence and/or contraction of the bladder. An electrode is then positioned, either surgically or percutaneously, at least in close proximity to the nerve and selectively energized to stimulate the nerve. Although the operative procedures, methods and systems hereinafter described are particularly applicable to controlling bladder and related functions, it should be understood that such procedures, methods and systems will also concurrently effect control of other organs, such as the bowel, colon and associated sphincters, (e.g., anus) and cuffs. In particular, when a specific operative procedure is followed to control bladder contraction and continence, the affected nerve or nerves will concurrently control other associated functions, such as bowel evacuation. Further, this invention contemplates either permanent surgical implantation or temporary percutaneous implantation for nerve stimulation purposes.

As further illustrated in FIG. 1, the main nerve supply emanating from each sacral segment S2, S3 and S4 comprises two components or roots, namely, a dorsal root D and a ventral root V. The dorsal root is primarily sensory to transmit sensation to the spinal cord whereas the ventral root is primarily motor to trasmit motor impulses from the spinal cord to bladder B and associated sphincter. Although illustrated as being separated, the dorsal and ventral roots for each nerve are, in fact, normally joined together and their fibers mixed to progress as a single trunk.

Fibers of the nerve trunk are divided into somatic fibers S which connect to voluntary muscles and autonomic fibers A that connect to visceral organs, such as bladder B. One of the novel aspects of this invention constitutes the separation or isolation of various components of these nerve fibers at various levels in the nervous system. For example, dorsal root D is desirably separated from ventral root V since this aspect of the invention primarily contemplates stimulating only the motor fibers of a particular ventral root. In this manner, the motor fibers can be stimulated without inducing pain and without generating impulses along the sensory passage way.

Somatic nerves S and autonomic nerves A can also be separated from each other. For example, in a particular application wherein it is desirable to only drive muscles controlled by the somatic nerve, the somatic nerve can be solely stimulated. Should it prove desirable to control the muscles of only a visceral organ, such as the detrusor muscle of bladder B, the autonomic nerve fibers could be stimulated. Stimulation of the entire nerve trunk would function to stimulate each of the dorsal, ventral, somatic and automatic fibers.

However, such stimulation would prove undesirable in most applications since uncoordinated action would ensue, e.g., bladder B and external sphincter E would each contract and no effective response to stimulation would be realized. Thus, the ability to isolate the dorsal and ventral roots from each other and to further isolate the autonomic nerves from the somatic nerves enables a practitioner to alleviate pain and to simultaneously achieve specific responses of the controlled organ or organs.

For example, responses obtained with pre-operative evaluation of responses to stimulation recorded urodynamically could indicate that the S2 sacral nerve constitutes the main motor supply to external sphincter E, whereas the S3 sacral nerve constitutes the main motor supply to bladder B. Thus, the S3 sacral nerve would be utilized to control the detrusor muscle and thus the contracting function of bladder B alone, whereas the S2 sacral nerve would be utilized to control the muscles controlling the continence function of external sphincter E. Studies have shown that in certain patients, only the nerves on one side of the sacrum provide the main motor control over a particular organ, i.e., unilateral control rather than bilateral control. Pre-operative testing of a particular patient will determine which variation will provide the best choice for a subsequent operative procedure. The ability of this invention to isolate various components of the various nerves, with the combined ability to test a patient intraoperatively and record responses, has enabled the applicants herein to isolate and selectively stimulate the particular nerve fibers that will effect the specific function or functions required.

FIGS. 1 and 3-11 hereinafter describe various combinations of operative procedures for effecting the desired neurostimulation for specific case studies (male or female). For example, a quadriplegic who has suffered a neck injury that damages the spinal cord will normally require an operative procedure wherein control of bladder B and external sphincter E are of utmost importance. In addition, the quadriplegic will suffer uncontrolled bowel evacuation, for example, which is concurrently controlled when bladder control is effected by such operative procedure. In addition, it may prove desirable to modulate other voiding dysfunctions that may occur as a result of one or more of a multitude of other neurological reasons.

Thus, it is emphasized that the specific operative procedures herein described can be combined with one or more of the other procedures described herein, as dictated by pre-operative evaluation of responses to stimulation recorded urodynamically. For example, when a particular procedure (e.g., electrode implant, nerve separation, sectioning, etc.) is described as being performed bilaterally, clinical testing may indicate that in certain other patients, a unilateral procedure is necessary (and vice versa). Likewise, the specific steps or procedures utilized in one operative procedure (FIGS. 1 and 3-11) may be utilized in combination with one or more steps utilized in other operative procedures, as will be appreciated by those skilled in the arts relating hereto.

As suggested above, although the operative procedures herein described are primarily useful and applicable to control of bladder functions, such procedures are concurrently applicable to the control of other organs, including the bowel and colon, associated sphincters (e.g., anus) and cuffs. In all of the following operative procedures, it is assumed that pre-operative evaluation of response to stimulation has been recorded urodynamically to precisely locate the nerves requiring separation, neurostimulation and/or isolation, such as by sectioning.

OPERATIVE PROCEDURE FOR CONTROLLING BLADDER EVACUATION (FIG. 1)

FIG. 1 illustrates an operative procedure whereby continence and evacuation of bladder B is closely controlled in a particular patient, such as a quadriplegic. It should be again understood that the particular operative procedure utilized will depend upon a particular patient's ability to respond to electrical stimuli at strategic locations on his or her nervous system in the pelvic plexus region. For example, it is assumed in the FIG. 1 operative procedure that the patient is unable to self-control his or her bladder functions and that such locations have been evaluated pre-operatively.

Figure 5:
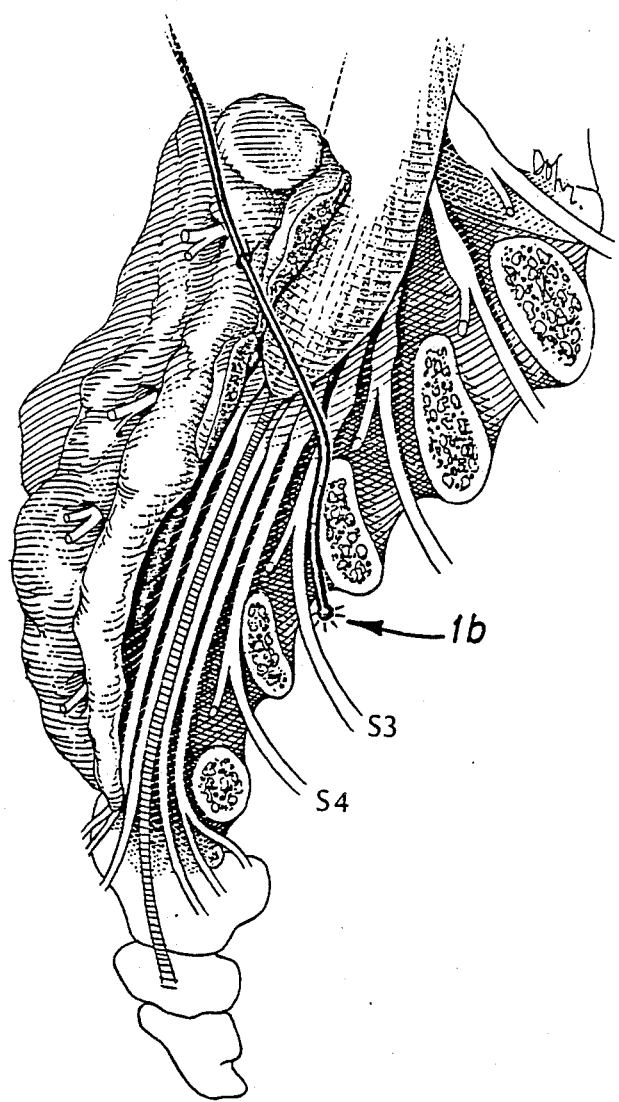
FIG. 5 schematically illustrates the percutaneous implantation of an electrode adjacent to the S3 sacral nerve through the dorsum for the purpose of selectively stimulating such nerve.

As shown in FIG. 1, after the anatomical location of the S3 sacral nerve is identified, such as by the percutaneous insertion and electrical energization of an electrode placed at least in close proximity to such nerve, as illustrated in FIG. 5, the dorsal (sensory) root D and ventral (motor) root V are surgically separated bilaterally on each side of sacral segment S3. An electrode 2 is then attached by sutures and implanted on each ventral root V for purposes of external excitation and stimulation, as hereinafter described with reference to the type of micturition control system illustrated in FIG. 12.

After bilateral implantation of electrodes 2 on ventral components or roots V, each superior somatic nerve $S_s$ is sectioned at 3 bilaterally to eliminate any increase in the resistance normally provided by the levator ani muscles at least partially surrounding external sphincter E and controlled by superior somatic nerve $S_s$. Superior somatic innervation ($S_s$) is commonly described in anatomy books (e.g., CIBA or Gray's) as part of the innervation to the levator ani muscles, whereas inferior somatic innervation ($S_I$) is classically described as the pudendal nerve in Alcock's Canal. It should be noted that an internal sphincter I will normally open automatically when the bladder contracts and thus requires no artificial control.

Applicants are unaware of any prior art teachings suggesting the above operative procedure, including identification and separation of dorsal root D from ventral root V, the use of electrode 2 on at least one ventral root for the purpose of selectively controlling the motor functions of the bladder or the identification and isolation of superior somatic nerve $S_s$ and its role in increasing the resistance to the flow of urine from the bladder at external sphincter E when the bladder is contracting for evacuation purposes.

As suggested above, the operative procedure in FIG. 1 was preceded by identification of the S3 sacral nerve and confirmation that it controlled bladder and related functions by use of intraoperative stimulation and urodynamic recordings. Minimum requirements to effect bladder evacuation without sacrificing continence, i.e., the ability to retain contents of the bladder until conditions are proper for urination, were assumed to be confirmed. The subsequent bilateral separation of ventral root V from dorsal root D and the bilateral implantation of electrode 2 on the ventral root was found to minimize risk of pain or other undesirable reflexogenic response. As described above, outlet resistance through urethra U was insured by sectioning superior somatic nerve $S_s$ at 3 whereby the various nerves controlling outlet resistance at external sphincter E were totally isolated, i.e., isolation of motor supply to levator ani.

Pre-operative electrostimulation was achieved by the use of a bipolar probe for stimulating the various nerve bundles. A nerve stimulator was then used to deliver a DC square wave for stimulation purposes. The nerve stimulator may be of the type manufactured by Grass medical instruments of Quincy, Mass., under Model No. S-44. The electrodes may be of the type disclosed in U.S. patent application Ser. No. 597,502 for "Method and Pacemaker for Stimulating Penile Erection," filed on Apr. 6, 1984 and assigned to the assignee of this application. For example, each electrode may constitute a bipolar cuff electrode having an inside diameter approximating 3–5 mm. and provided with 1 mm. by 2 mm. platinum contacts having a 3 mm. separation placed opposite each other about the periphery of ventral nerve root V. This type of electrode is manufactured by Avery Laboratories, Inc. under Model No. 390.

As described more fully hereinafter in reference to FIGS. 12–17, suitable receivers in the form of implantable silastic-coated units containing an antenna coil, adapted to receive RF (radio frequency) pulses from an external transmitter, are implanted subcutaneously in the patient to transmit pulses to the electrodes to control bladder evacuation in a controlled manner.

OPTIONAL OPERATIVE PROCEDURE FOR CONTROLLING BLADDER EVACUATION (FIG. 3)

FIG. 3 illustrates optional variations to the FIG. 1 operative procedure which will potentially enhance bladder evacuation. After the various critical nerves for controlling bladder evacuation have been identified by intraoperative stimulation and urodynamic recordings, each of the S2, S3 and S4 sacral nerves are separated to isolate the respective ventral and dorsal roots thereof. Pudendal or inferior somatic nerve $S_I$ is then sectioned unilaterally to isolate external sphincter E on one side. Dorsal root D of the S3 sacral nerve is then sectioned at 2a to thus isolate the sensory function thereof. Although illustrated as being performed unilaterally, and as stated above, in certain applications it may prove desirable to perform such sectioning bilaterally.

An electrode 3a is then implanted on the entire S3 sacral nerve unilaterally, with or without dorsal rhizotomies at other sacral levels. The S3 sacral nerve is then sectioned at 4a unilaterally (or bilaterally), downstream of pelvic nerve P to isolate this nerve's contribution to inferior somatic nerve $S_I$. It should be noted that electrode 3a is thus positioned on the S3 sacral nerve to stimulate the detrusor muscles of bladder B, via pelvic nerve P.

After appropriate separation of the dorsal and ventral roots of the S2 sacral nerve, the dorsal root is sectioned at 5a unilaterally (or bilaterally) and an electrode 6a is suitably implanted on the ventral root V of the S2 sacral nerve. It should be noted that superior somatic nerve $S_s$ is preferably sectioned bilaterally, as described above in reference to the FIG. 1 operative procedure, to eliminate any additional increase in resistance from contradiction of the levator ani muscle when the bladder is contracting the evacuation purposes.

The above options will also tend to eliminate or minimize a response in the pelvic floor sphincter which would otherwise prevent low resistance voiding of the bladder synchronous with stimulation. These optional variations address the possibility that excessive residual sphincter activity remains with stimulation after the FIG. 1 operative procedure has been attempted. Sphincter response may be reflexly produced which suggests the need for dorsal sectioning at 2a and 5a in FIG. 3, or directly produced to suggest sectioning 1a of inferior somatic $S_I$, unilaterally or bilaterally. The above steps must, of course, be carefully evaluated prior to the selected operative procedure so as not to compromise continence or the contraction of the bladder or bowel or nerves controlling the erection process.

Additional optional procedures may include percutaneous implantation of an electrode 7a' on sacral nerve S3 and/or S4, upstream of the point whereat the autonomic nerve roots forming pelvic nerve P separate from the respective sacral nerve proper, to aid in bladder contraction through the pelvic nerve. A further option contemplates implantation of a cuff electrode 8a' around sacral nerve S4, either unilaterally as shown or bilaterally, to assist in the control of bladder evacuation. It should be understood that above sectioning steps 2a and 5a, as well as the implantation of electrodes 3a, 6a and 8a', require laminectomy, i.e., incision of the posterior arch of the vertebrae.

NON-LAMINECTOMY PROCEDURE FOR CONTROLLING VISCERAL ORGANS (FIGS. 4 AND 5)

Figure 4:
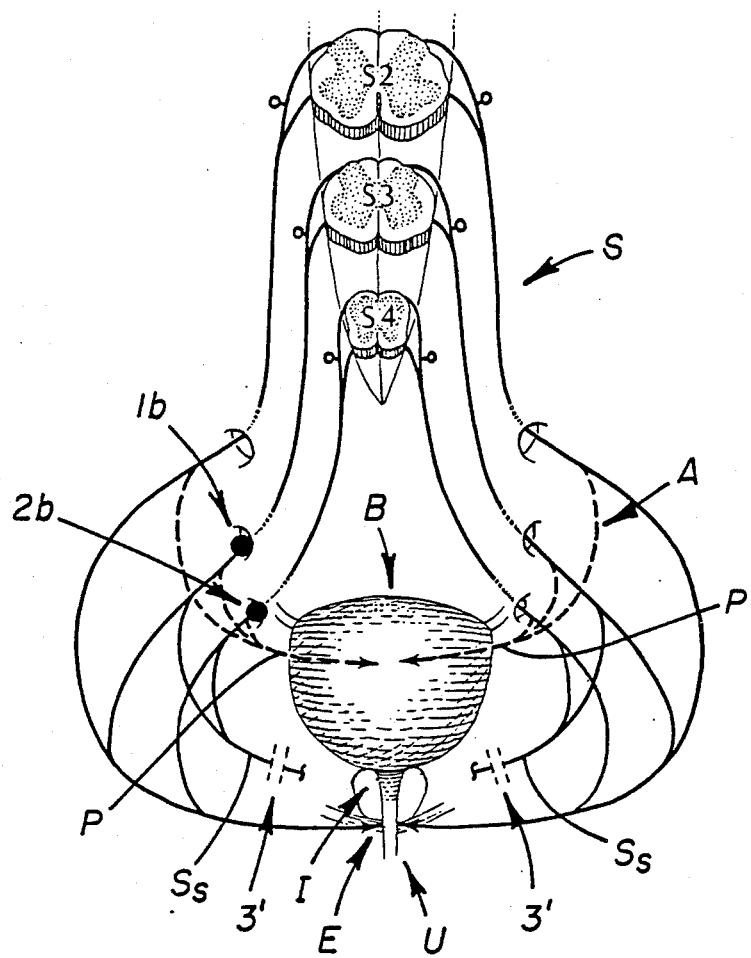

FIG. 4 illustrates an operative procedure wherein an electrode 1b is implanted onto the S3 sacral nerve through a sacral foramen without excising the posterior arch of the vertebrae. A second electrode 2b may be implanted in a like manner on the S4 sacral nerve, either in addition to or in lieu of electrode 1b. These electrode implants may be effected unilaterally, as illustrated, or bilaterally, depending on the pre-operative test results. Optionally, superior somatic nerve $S_s$ is sectioned at 3', either unilaterally or bilaterally as illustrated in FIG. 4.

The system thus effected by the FIG. 4 operative procedure will normally provide means for selectively eliminating or suppressing spastic detrusor activity, spastic urethral and pelvic floor activity and spastic anal sphincter. Such system may further suppress or enhance erection.

FIG. 5 illustrates the percutaneous implantation of electrode 1b through the dorsum and the sacral foramen of sacral segment S3 for the purpose of selectively stimulating the S3 sacral nerve. As described in above-referenced U.S. patent application Ser. No. 597,502, after the appropriate depth and location of the S3 nerve has been verified by electrostimulation and recorded urodynamically, electrode 1b can be inserted through the hollow spinal needle used for such stimulation with the wire lead connected to the electrode being suitably sutured in place, as shown, for attachment to a receiver (not shown), as will be described more fully hereinafter. This percutaneous method can also be used to temporarily implant an electrode on any one or more of the sacral nerves for testing purposes, i.e., to record activity in the bladder in response to stimulation of one or more of the nerves by the electrodes to thus determine which nerve or nerves are controlling the bladder functions. This procedure can be conducted unilaterally or bilaterally.

For example, electrode 1b could be percutaneously placed on the S3 sacral nerve with the external extremity of the wire attached to the electrode than being taped to the skin, along with a receiver connected thereto. The patient could then resume his day-to-day lifestyle and be allowed to stimulate the nerve or nerves artificially via a transmitter compatible with the receiver. If the response is positive and complete relief is achieved, the electrode or electrodes could be permanently implanted or temporarily implanted for the purpose of correcting any dysfunction by "retraining" the nerve and associated muscles. Should little or no improvement result, the same procedure could be followed to accurately ascertain which nerve or nerves require stimulation. Thus, this invention contemplates not only the implantation of one or more electrodes in the sacral nervous system for controlling evacuation of a visceral organ or the like, but also contemplates use of such electrodes and procedures to rehabilitate muscle dysfunction by neuromodulation of muscular behavior.

ADDITIONAL OPTIONAL OPERATIVE PROCEDURES (FIGS. 6–11)

Figure 6:
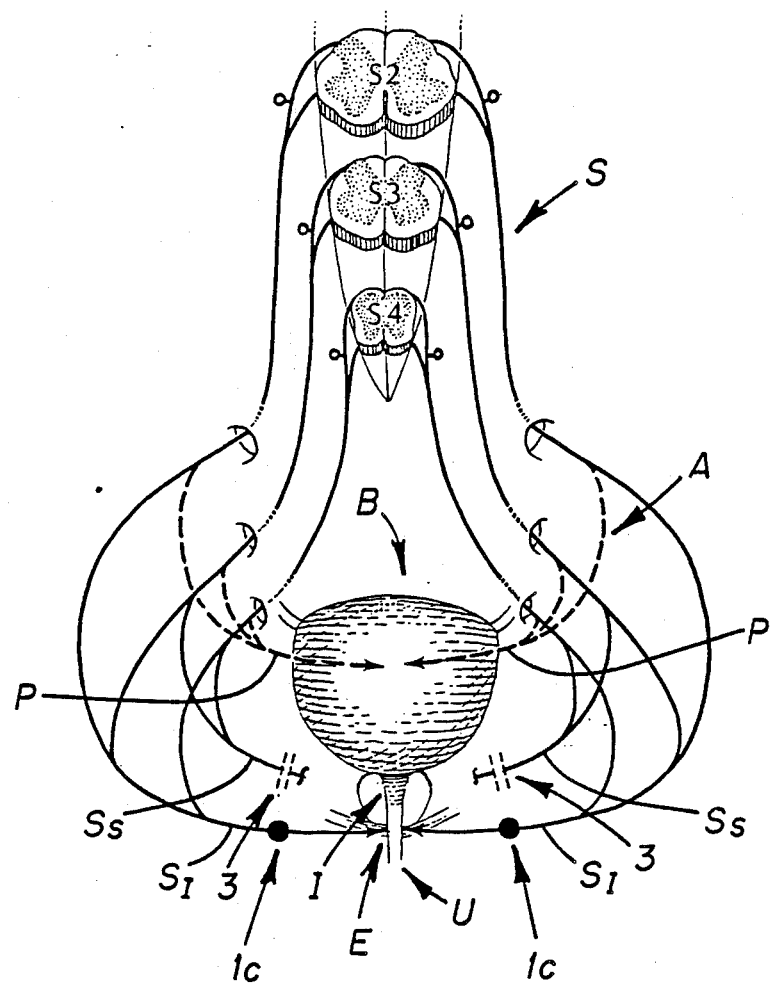
FIGS. 6-11 are views similar to FIG. 1, but illustrate additional operative procedures for controlling bladder evacuation and related functions.

FIG. 6 illustrates an optional variation for controlling evacuation of bladder B. In particular, superior somatic nerve Ss is sectioned at 3, either unilaterally or bilaterally, as shown. In addition, electrodes 1c are implanted on inferior somatic nerve $S_I$, also unilaterally or bilaterally, depending on the response obtained from preoperative evaluation of responses to stimulation recorded urodynamically.

Figure 7:
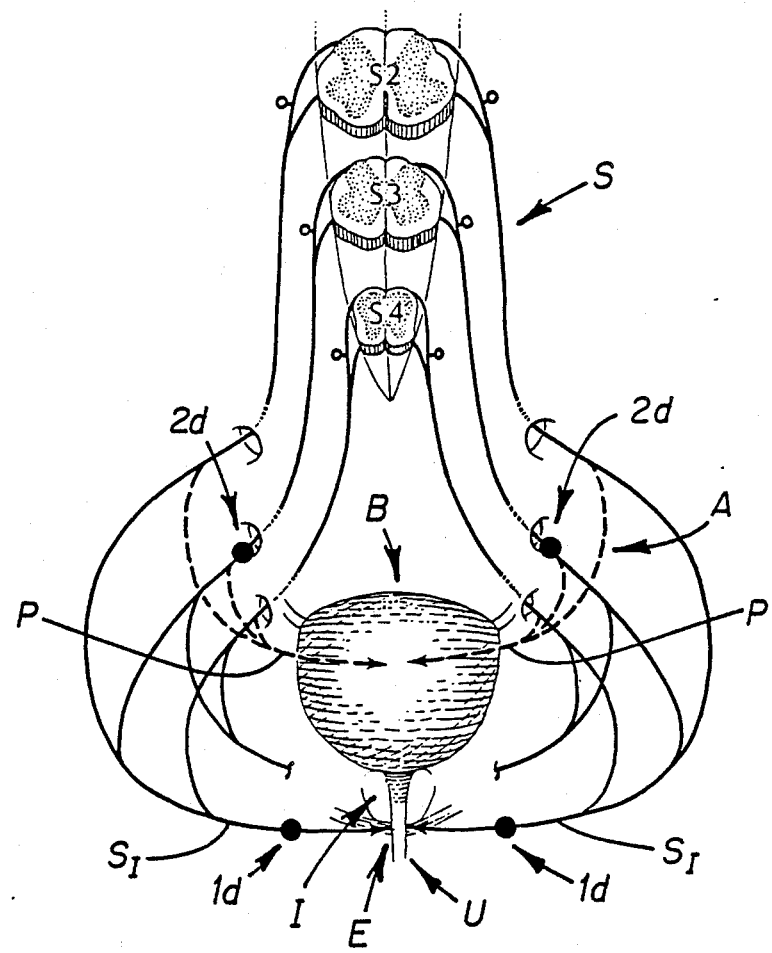
Figure 8:
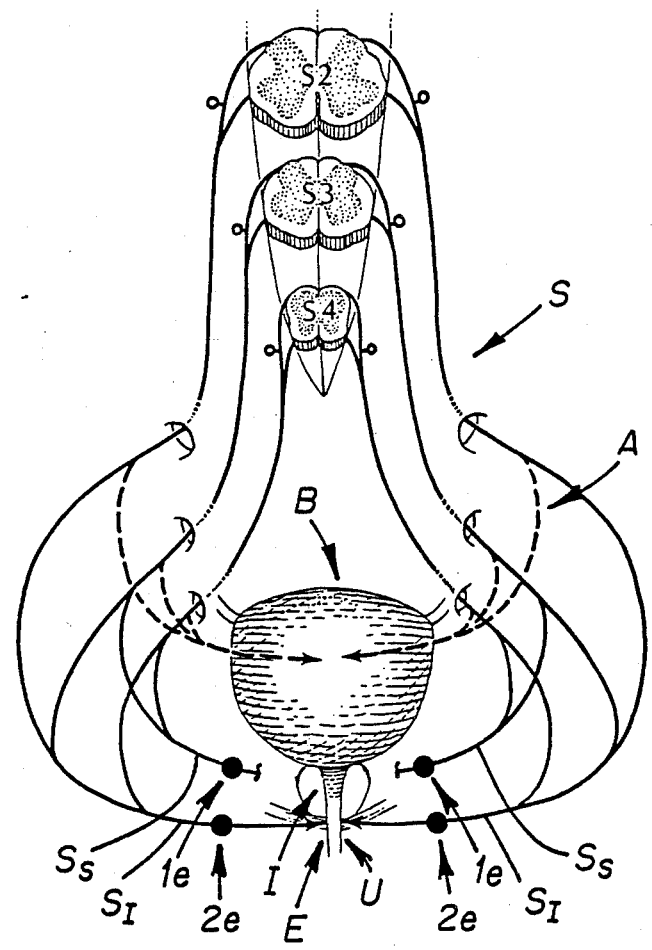

In FIG. 7, electrodes 1d are implanted bilaterally on inferior somatic nerve $S_I$ and electrodes 2d are implanted bilaterally on the S3 sacral nerve percutaneously. In FIG. 8, electrodes 1e are implanted bilaterally on superior somatic nerve $S_s$ and electrodes 2e are implanted bilaterally on inferior somatic nerve $S_I$.

Figure 9:
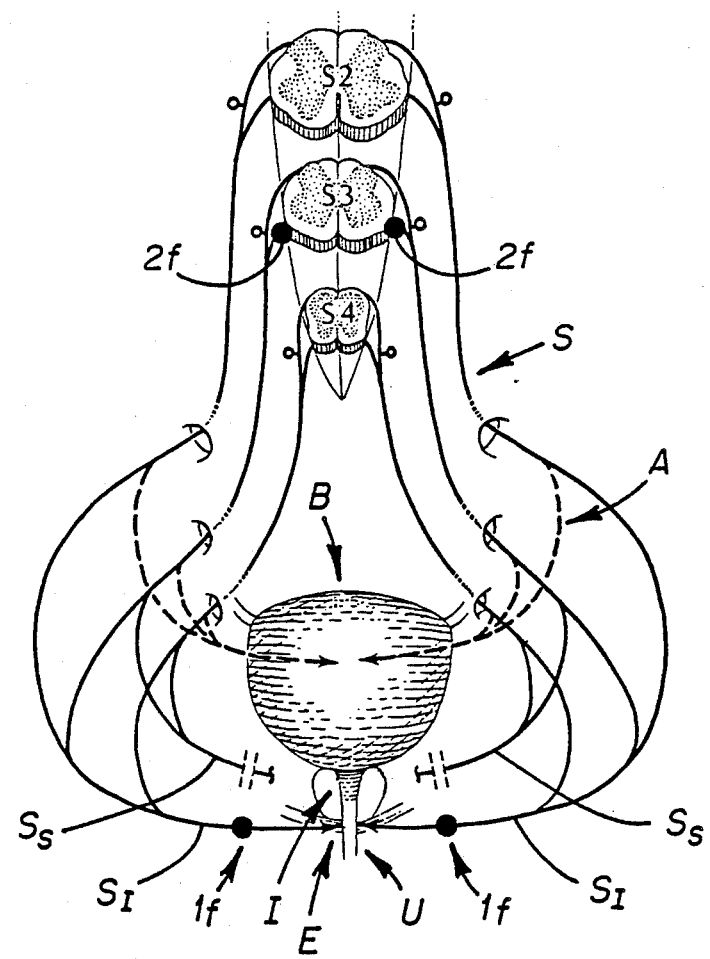

FIG. 9 illustrates another operative procedure for controlling continence and bladder contraction. In the illustrated operative procedure, electrodes 1f are implanted bilaterally on inferior somatic nerve $S_I$. Superior somatic $S_s$ is sectioned bilaterally, as illustrated, and a pair of second electrodes 2f are implanted bilaterally on the separated ventral root V of the S3 sacral nerve.

Figure 10:
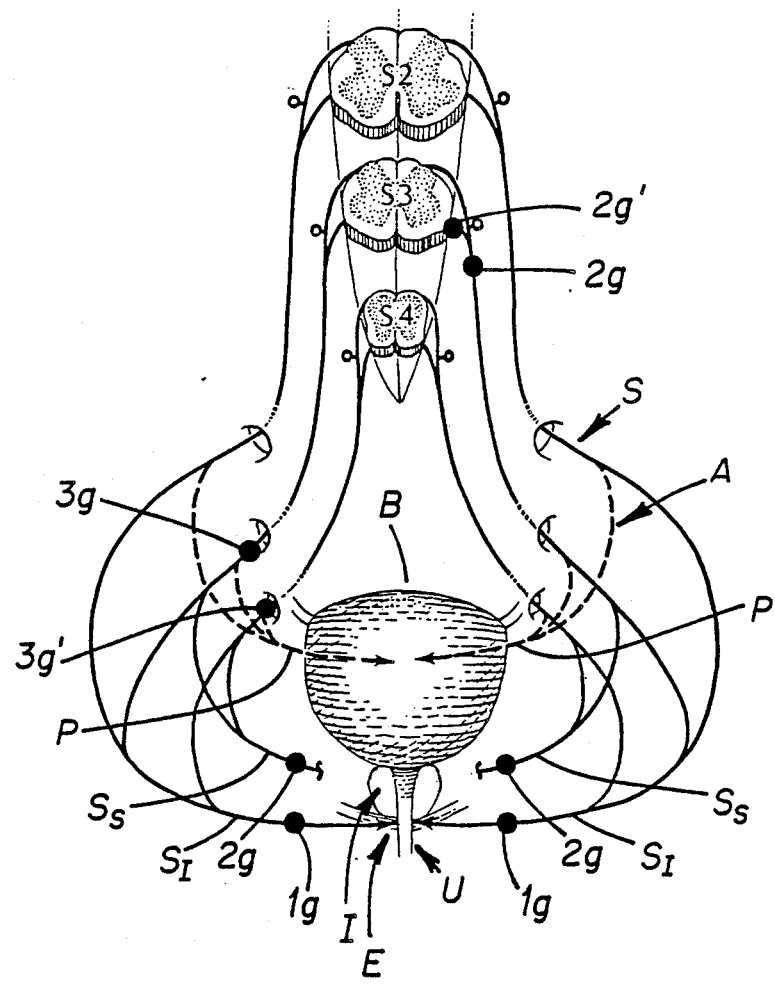

FIG. 10 illustrates an operative procedure particularly adapted for achieving continence due to muscle weakness of the bladder or bowel. Electrodes 1g and 2g are implanted bilaterally on inferior somatic nerve $S_I$ and on the S3 sacral nerve, as illustrated. As an option to implantation of the electrode unilaterally on the S3 sacral nerve, an electrode 2g' could be implanted on the ventral root thereof. In addition, an electrode 3g is implanted unilaterally on the S3 sacral nerve percutaneously. Alternatively, an electrode 3g' could be implanted on the S4 sacral nerve, also percutaneously.

As another option, illustrated in FIG. 10, another electrode 2g could be implanted on superior somatic nerve $S_s$, either unilaterally or bilaterally, as illustrated. The FIG. 10 operative procedure illustrates the two components of sphincter contraction with the number of implants and their locations being dependent on recruitability of muscle activity in individual patients and/or the ability of percutaneous technique to adequately couple the electrodes with the appropriate nerve fibers.

Figure 11:
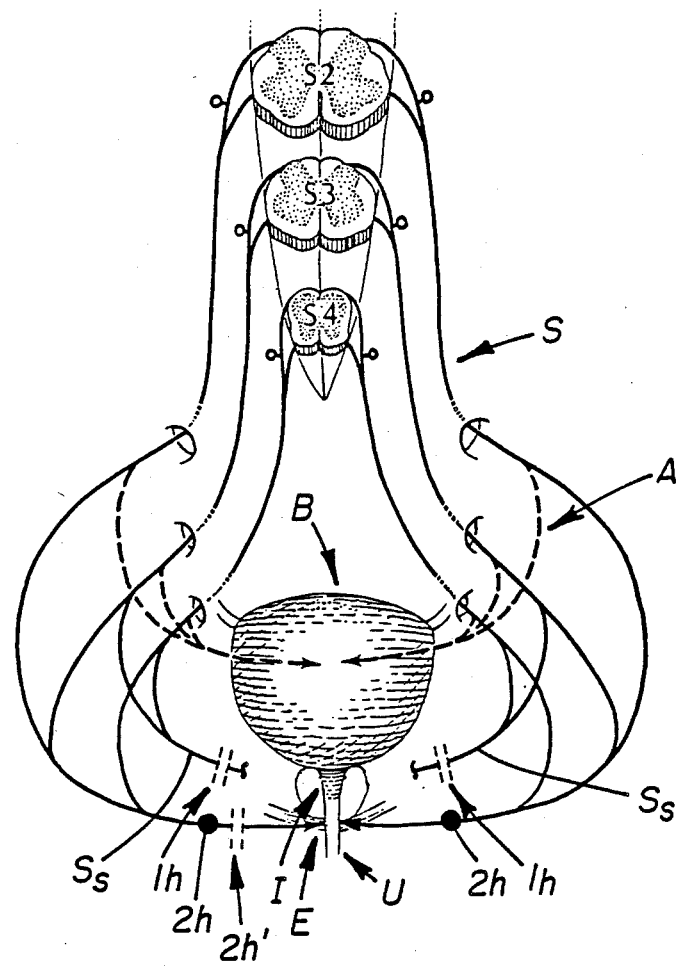

FIG. 11 illustrates an operative procedure particularly adapted for controlling autonomic dysreflexia and bladder storage. Superior somatic nerve $S_s$ is sectioned bilaterally at 1h and electrodes 2h are implanted on the inferior somatic nerve bilaterally. Alternatively to the latter step, electrode 2h could be implanted unilaterally with the opposite side of the inferior somatic nerve being sectioned at 2h'.

As suggested above, the operative procedures illustrated in FIGS. 1 and 3–11 are suggestive of specific procedures applicable to particular patients. Thus, the various steps described above in connection with one particular procedure could be included with or substituted in lieu of steps included in one or more of the other procedures to meet a particular case study. For example, many of the above steps could be performed bilaterally where disclosed unilaterally, and vice versa.

It follows that the claims appended hereto, when reciting the method steps of "implanting" or "attaching" an electrode to a particular nerve or "sectioning" a particular nerve, etc., intend to cover both unilateral and bilateral procedures.

Selection of the various options described above would be based upon evaluation of responses obtained from preoperative stimulation recorded urodynamically. The ability of a particular procedure to be conducted percutaneously or surgically, or a combination thereof, further expands application of this invention. Those skilled in the medical arts relating hereto will also appreciate that the above operative procedures may be utilized to control not only bladder functions but also concurrently central functions of other organs, such as the colon, bowel, anal sphincter, etc.

DESCRIPTION OF MICTURITION CONTROL SYSTEM (FIGS. 12–14)

Figure 12:
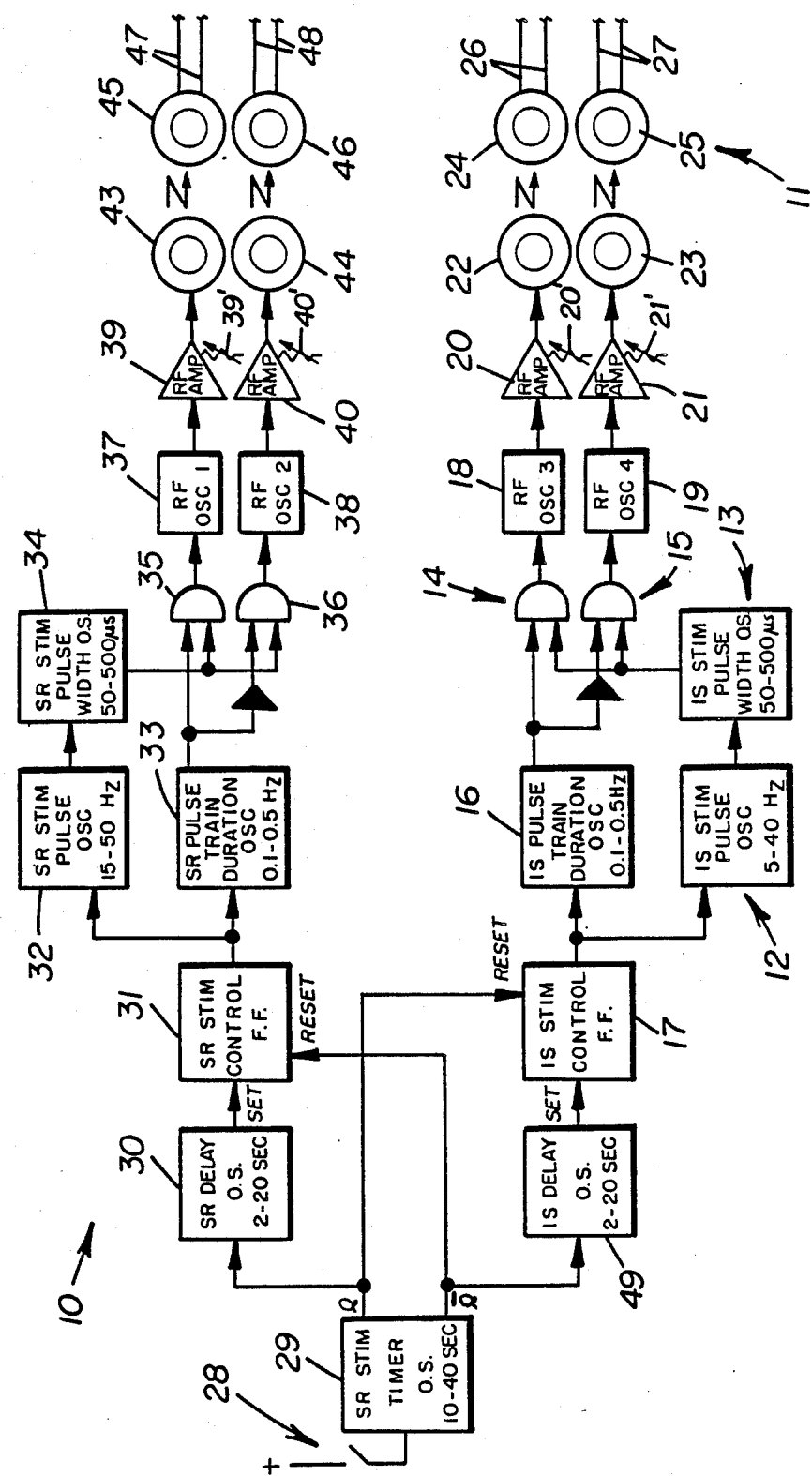
FIG. 12 illustrates a micturition control system adapted for use in conjunction with an operative procedure for controlling bladder evacuation and related functions.

FIG. 12 illustrates a micturition control system adapted to transmit electrical current (radio frequency) pulses to electrodes implanted on selected nerves of the above-described systems, such as the implantation illustrated in FIG. 9, i.e., leads 26 and 27 connected to electrodes 1f and leads 47 and 48 connected to electrodes 2f. The control system comprises an external control-transmitter system 10, and a receiver system 11 implanted on a patient for transmitting electrical current pulses to the electrodes. The two-fold purpose of this system is to efficiently (1) maintain urethral tone and hence continence of urine until bladder voiding is desired; and (2) provide bladder contraction and voiding on demand by a patient or his attendant, for patients having bladder or pelvic problems or paralysis.

FIG. 12 illustrates the electronic control, transmitter and receiver components of the system whereas FIG. 14 illustrates the types of signals and their time relationship in the electronic control component of the system. The symbol SR as used herein depicts a component of the control system connected to an electrode implanted on a particular sacral nerve or root, whereas IS depicts connection to inferior somatic nerve $S_I$, controlling continence.

The ongoing control of continence (retaining the contents of bladder B) is provided by stimulation of a selected nerve or nerves as described above. This control function is accomplished by the ongoing stimulation produced by a stimulus pulse oscillator 12 (OSC) and associated circuits. The oscillator, preferably operating at a rate within the range of from 5 to 40 pulses per second, emits a square wave output signal that drives an IS stimulus pulse width one-shot (O.S.) 13 which produces signal pulses with widths within the range of from 50 to 500 microseconds, as illustrated in FIG. 14. These pulses are controlled by AND gates 14 and 15 to produce separate trains of pulses, also shown in FIG. 14. Gating is produced by an IS pulse train duration oscillator 16. It should be noted in FIG. 12 that the two phases of the square wave output of oscillator 16 can be obtained by the illustrated inverter circuit.

The frequency of the square wave output of oscillator 16 is preferably selected from within the range of from 0.1 to 0.5 Hertz (cycles per second). This oscillator is controlled by an IS stimulus control flip-flop 17. When the flip-flop is set, it allows oscillator 16 to run to enable gates 14 and 15 to transmit signal pulses (FIG. 14) to turn on and off radio frequency (RF) generators or oscillators 18 and 19. Radio frequency amplifiers 20 and 21, whose output amplitudes are adjustable by variable resistors 20' and 21', respectively, receive the separate pulses to drive antennas 22 and 23.

The antennas are inductively coupled to receivers 24 and 25 which detect the separate sets of RF pulses and transmit such detected pulses to a particular nerve-implanted electrodes via electrical leads 26 and 27, respectively. Receivers 24 and 25, as well as hereinafter described receivers 45 and 46, are each subcutaneously implanted on a particular patient in the manner described in above-referenced U.S. patent application Ser. No. 597,502.

When it is desired to evacuate bladder B, and assuming that the four energized electrodes are properly implanted for a particular patient in the manner described above, the patient or his attendant will momentarily close a switch 28. Transmitter 10 and attendant antennas 22 and 23 are, of course, suitably housed as an external unit, readily accessible to the patient. The closing of switch 28 will activate an SR stimulus timer 29 for a selected length of time, preferably within the range of from 10 to 40 seconds.

During this time interval, the output Q of timer 29 goes high to activate an SR delay oscillator 30 and resets IS stimulus control flip-flop 17 so that it turns off the IS pulse train duration oscillator 16. As a consequence, stimulation of the urethral sphincter closure, for example, is disabled. Simultaneously therewith, the $\overline{Q}$ output of timer 29 goes low to allow flip-flop 31 to be set on a signal from SR delay 30. After a predetermined and selected time delay of from 2 to 20 seconds (FIG. 14), for example, the output signal from SR delay 30 sets a flip-flop 31 which then starts an SR stimulus pulse oscillator 32 and SR pulse train duration oscillator 33.

Oscillator 32 will generate a square wave signal that is preferably selected from the range of from 15 to 50 Hertz, as diagramatically illustrated in FIG. 14. The output from oscillator 15 then drives an SR stimulus pulse width O.S. 34 which produces signal pulses at a selected width of from 50 to 500 microseconds. These pulses are ANDED by gates 35 and 36 with the output of oscillator 33 to produce trains of pulses, as illustrated in FIG. 14. It should be noted in FIG. 12 that the opposite phases of the square wave output of oscillator 33 may also be obtained by the use of the illustrated inverter circuit. Gate control originates at oscillator 33 which has a selected frequency within the range of from 0.1 to 0.5 Hertz.

The pulse trains from AND gates 35 and 36 control RF oscillators 37 and 38, respectively. These are turned on when the pulses are high. The RF signals are amplified in RF amplifiers 39 and 40 wherein the output amplitudes are controlled by variable resistors 39' and 40', respectively. The outputs of the amplifiers drive antennas 43 and 44 which inductively couple the signal through the patient's skin and to implanted receivers 45 and 46. The receivers detect the RF pulses and transmit the stimulus pulses to the particular implanted electrodes, via electrical leads 47 and 48.

At the end of the selected time period, e.g., 10 to 40 seconds, of timer 29, the output reverses, as illustrated in FIG. 14. The Q output goes low and enables flip-flop 17 to activate oscillator 16 when the "set" signal is transmitted from IS delay O.S. 49. The $\bar{Q}$ output of timer 29 goes high and activates 49. At the end of the preselected time delay of from 2 to 20 seconds, the output (FIG. 14) sets IS stimulus control flip-flop 17 which then restarts the continence stimulus circuitry until bladder evacuation is again required. The $\bar{Q}$ output from timer 29 also resets flip-flop 31 and thus disables oscillators 32 and 33 to end the bladder voiding stimulation.

With regards to the micturition control system just described, the receivers 24 and 25, leads 26 and 27 and electrodes 1f comprise a first stimulation system for stimulating the external sphincter functions while receivers 45 and 46, leads 47 and 48 and electrodes 2f comprise a second stimulation system for stimulating the bladder functions. Elements 12–16 and 18–23 comprise a first pulse generating and transmitting means for generating and transmitting series of electrical pulses to the receivers 24 and 25 of the first stimulation system, while elements 32–40, 43 and 44 comprise a second pulse generating and transmitting means for generating and transmitting series of pulses to the receivers 45 and 46 of the second stimulation system. 57, in conjunction with coil 56, provides a tuned circuit that is tuned to one of the four different frequencies of the transmitter. The other three receivers are tuned to their respective transmitting frequencies when the system uses four separate radio frequencies. Alternatively, the frequencies may be the same for all four transmitters with the four receivers being tuned to the same transmitting frequency. In the latter application, the four transmitting antennas and the four implanted receivers must be separated so that the signal in any one transmitting antenna will not provide false signals in the other three receivers.

Still referring to FIG. 13, a diode 58 detects, by half-wave rectification, the pulsed stimulus current from the RF bursts. Resistors 59 and 60 and capacitors 61 and 62 function to filter the RF out of the stimulus signal which is lead to the nerve electrodes via electrical leads, described above. Maximum stimulation of the nerves is achieved when the negative pole is attached to the distal electrode contact on the nerve and the corresponding positive pole is the proximal contact of the nerve electrode assembly.

Those skilled in the art will appreciate that the FIG. 12 control system can be suitably modified to control the energization of the electrodes used in the above-described procedures and variations thereof. For example, only the portion of the system for controlling pulse inputs to antennas 24 and 25 could be utilized to energize electrodes 2 in FIG. 1.

Figure 17:
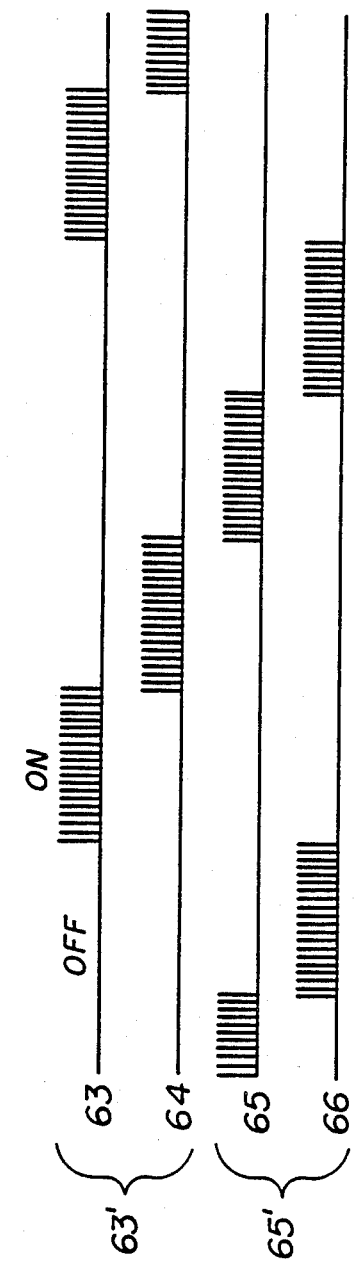
FIG. 17 diagrammatically illustrates electrical impulses in their timed relationship for the electrode arrangements illustrated in FIGS. 15 and 16.

FIGS. 15 and 16 illustrate typical electrode implantations for stimulation purposes. FIG. 17 diagramatically illustrates the timing of stimulus pulse trains to electrode pairs with each electrode contact being activated essentially 100/n % of the time for n active (cathodol) contacts.

One of the primary problems encountered with prolonged and continuous electrical stimulation of a nerve and muscle system to achieve chronic on-going muscle contractions is fatigue of the nerve and associated muscles. One way to prevent or prolong the onset of fatigue (the muscle being more susceptible to fatigue than the nerve) is to stimulate the system in a non-continuous and time-modulated format. Otherwise stated, alternate stimulation of different groups of fibers in a nerve system with short bursts of stimulus pulses provides such desiderata. This method of stimulation allows the muscles and nerves to recover between trains of stimuli while other nerves and muscles are being activated to continue the desired physiological effect.

Time-modulation of stimuli to nerves to achieve muscle contraction, for example, can be accomplished in at least two ways. FIGS. 15 illustrates a first approach wherein a multiplicity of electrode pairs 63, 64 and 65, 66 are attached to separate nerve bundles. Each pair of electrodes are activated so that each electrode is "on" for only a portion of a particular stimulation cycle, e.g., with four electrode pairs, each would be stimulating its nerve bundle approximately one-quarter of the time (in general, 100/n % of the time for n electrode pairs). It should be noted in FIG. 17, although shown in coincidence, that an overlap or dead time can be effected between the stimuli trains.

FIG. 16 illustrates a second approach to accomplish time modulation of nerve stimulation wherein a multiplicity of active electrode contacts are employed on a single electrode. However, in order to achieve this alternating stimulation on a single nerve bundle, the intensity of the stimulus pulses must be sufficiently low so that all nerve fibers are not stimulated by a single active electrode contact. Nonetheless, the amplitude of the stimulus pulses must be sufficiently high so that the desired physiological function can be achieved.

The active electrodes (cathodes) must be located on the nerve bundle so that they (stimulate) different nerve fibers, Thus, a single electrode is not activating all of the fibers in associate muscles, as illustrated in FIGS. 16 and 17. Ideally, each electrode contact would function to activate the proper proportional number of fibers, e.g., in the case of two contacts, each contact would activate one-half of the fibers and in the case of four contacts, each contact would activate one-quarter of the fibers, etc. However, the desired physiological function must be achieved when a single contact is used on that particular nerve bundle. An exception, of course, would be in applications wherein other nerve bundles are similarly connected to a similar time-modulated system. In the latter application, partial nerve stimulation from the combined group of stimulated nerve bundles would accomplish the desired physiological results.

We claim:

1. An electronic control system for sending stimulation signals to first and second stimulation implanted in a body, said stimulation systems each including at least one receiver and an electrode associated with said receiver, the electrode of said first stimulation system being positioned on a nerve controlling one bodily function and the electrode of said second stimulation being positioned on a nerve controlling another bodily function, the electronic control system comprising:

a first pulse generating and transmitting means for generating and transmitting a series of electrical pulses to the receiver of said first stimulation system, a second pulse generating and transmitting means for generating and transmitting a series of electrical pulses to the receiver of said second stimulation system, a manually operable member, means for turning off said first pulse generating and transmitting means in response to operation of said manually operable member, and, after a first preselected time delay, for turning on said second pulse generating and transmitting means, means operable at a selected time period after turning on of said second pulse generating and transmitting means for turning off said second pulse generating and transmitting means and, after a second preselected time delay, for turning back on said first pulse generating and transmitting means.

2. An electronic control system as set forth in claim 1, wherein each of said first and second pulse generating and transmitting means has the function of generating and transmitting time spaced bursts of pulses.

3. An electronic control system as set forth in claim 1, wherein said first stimulation system includes a second receiver and an electrode associated with said second receiver, the two electrodes of said first stimulation system being positioned on nerves both controlling said one bodily function, said electronic control system being further characterized in that said first pulse generating and transmitting means has the function of generating and transmitting a series of electrical pulses to the two receivers of said first stimulation system.

4. An electronic control system as set forth in claim 3, wherein said first pulse generating and transmitting means has the function of generating and transmitting time spaced bursts of pulses separately to each of the two receivers of the first stimulation system.

5. An electronic control system as set forth in claim 4, wherein said first pulse generating and transmitting means has the function of generating and transmitting the bursts of pulses alternately to the two receivers of the first stimulation system.

6. An electronic control system as set forth in claim 1, wherein said second stimulation system includes a second receiver and an electrode associated with said second receiver, the two electrodes of said second stimulation system being positioned on nerves both controlling said another bodily function, said electronic control system being further characterized in that said second pulse generating and transmitting means has the function of generating and transmitting a series of electrical pulses to the two receivers of said second stimulation system.

7. An electronic control system as set forth in claim 6, wherein said second pulse generating and transmitting means has the function of generating and transmitting time spaced bursts of pulses separately to each of the two receivers of the second stimulation system.

8. An electronic control system as set forth in claim 7, wherein said second pulse generating and transmitting means has the function of generating and transmitting the bursts of pulses alternately to the two receivers of the second stimulation system.

9. An electronic control system as set forth in claim 1, wherein said first stimulation system includes a second receiver and an electrode associated therewith, the two electrodes of said first stimulation system being positioned on nerves both controlling said one bodily function, and wherein said second stimulation system includes a second receiver and an electrode associated therewith, the two electrodes of said second stimulation system being positioned on nerves both controlling said another bodily function, said electronic control system being further characterized in that said first pulse generating and transmitting means has the function of generating and transmitting a series of electrical pulses to the two receivers of said first stimulation system, and said second pulse generating and transmitting means has the function of generating and transmitting a series of electrical pulses to the two receivers of said second stimulation system.

10. An electronic control system as set forth in claim 9, wherein said first pulse generating and transmitting means has the function of generating and transmitting time spaced bursts of pulses separately to each of the two receivers of the first stimulation systems, and wherein said second pulse generating and transmitting means has the function of generating and transmitting time spaced bursts of pulses separately to each of the two receivers of the second stimulation system.

11. An electronic control system as set forth in claim 10, wherein said first pulse generating and transmitting means has the function of generating and transmitting the bursts of pulses alternately to the two receivers of the first stimulation system, and wherein said second pulse generating and transmitting means has the function of generating and transmitting the bursts of pulses alternately to the two receivers of the second stimulation system.

* * * * *

UNITED STATES PATENT AND TRADEMARK OFFICE
CERTIFICATE OF CORRECTION

PATENT NO. : 4,703,755
DATED : November 3, 1987
INVENTOR(S) : EMIL A. TANAGHO, ET AL.

It is certified that error appears in the above-identified patent and that said Letters Patent is hereby corrected as shown below:

COL. 12, LINE 61, after "stimulation" insert --systems--.

COL. 12, LINE 66, after "stimulation" insert --system--.

Signed and Sealed this

Fifth Day of April, 1988

Attest:

DONALD J. QUIGG

*Attesting Officer*   Commissioner of Patents and Trademarks